(12) United States Patent
Abstreiter et al.

(10) Patent No.: US 6,870,235 B2
(45) Date of Patent: Mar. 22, 2005

(54) SILICON-ON-INSULATOR BIOSENSOR DEVICE

(75) Inventors: Gerhard Abstreiter, Garching (DE);
Marc Uwe Tornow, Garching (DE);
Karin Buchholz, Garching (DE);
Sebastian Markus Luber, Garching (DE); Erich Sackmann, Garching (DE); Andreas Richard Bausch, Garching (DE); Michael Gerold Hellmut Nikolaides, Garching (DE); Stefan Rauschenbach, Garching (DE)

(73) Assignee: Fujitsu Limited, Kawasaki (JP)

( * ) Notice: Subject to any disclaimer, the term of this patent is extended or adjusted under 35 U.S.C. 154(b) by 0 days.

(21) Appl. No.: 10/436,372

(22) Filed: May 13, 2003

(65) Prior Publication Data

US 2004/0007740 A1 Jan. 15, 2004

(30) Foreign Application Priority Data

May 15, 2002 (DE) ......................................... 102 21 799

(51) Int. Cl.[7] ........................................... H01L 29/786
(52) U.S. Cl. ........................... 257/414; 257/17; 257/20; 257/22; 257/347
(58) Field of Search ................................ 257/414, 347, 257/17, 20, 22

(56) References Cited

U.S. PATENT DOCUMENTS

| | | | | |
|---|---|---|---|---|
| 4,486,292 A | | 12/1984 | Blackburn | 204/416 |
| 5,719,033 A | * | 2/1998 | Ackley et al. | 435/7.92 |
| 5,814,280 A | * | 9/1998 | Tomita et al. | 422/82.01 |
| 6,294,133 B1 | * | 9/2001 | Sawada et al. | 422/82.01 |

FOREIGN PATENT DOCUMENTS

| | | |
|---|---|---|
| DE | 34 30 941 A1 | 3/1985 |
| DE | 40 28 062 A1 | 3/1992 |
| DE | 43 08 081 A1 | 9/1994 |
| DE | 100 06 760 A1 | 8/2001 |
| WO | WO 00/51180 | 8/2000 |

OTHER PUBLICATIONS

M. Huber et al.; ELSEVIER, Applied Surface Science 168, 2000, pp. 204–207.
Christine Berggren et al.; Electroanalysis 2001, 13, No. 3, pp. 173–180.
M. George et al.; ELSEVIER, Sensors and Actuators 86, 2000, pp. 187–196.
Yi Cui et al.; SCIENCE, vol. 293, Aug. 17, 2001, pp. 1289–1292.
Gavin MacBeath et al.; SCIENCE, vol. 289, Sep. 8, 2000, pp. 1760–1763.
M. J. Schöning et al.; Phys. Stat. Sol. (a) 185, No. 1, pp. 65–77, 2001.
British Office Action dated Nov. 10, 2003.
Newman et al., "Silicon–On–Insulator Integrated Optical Biosensors For Environmental Monitoring", Optical Techniques for Environmental Monitoring, IEEE Colloquium on, Nov. 15, 1995, pp. 3/1–3/6.
Yi et al., "A Novel Organophosphorous Pesticides Sensitive EN–FET", Solid–State Sensors and Actuators, 1991, Digest of Technical Papers, TRANDUCERS'91., 1991 International Conference on, Jun. 24–27, 1991, pp. 703–705.

* cited by examiner

Primary Examiner—Jerome Jackson
(74) Attorney, Agent, or Firm—Armstrong, Kratz, Quintos, Hanson & Brooks, LLP

(57) ABSTRACT

A Semiconductor sensor device for the detection of target molecules and molecular interactions, based on Silicon-on-Insulator (SOI) technology.

10 Claims, 4 Drawing Sheets

SOI Substrate

Sensing 'nano'-structures

SILICON-ON-INSULATOR BIOSENSOR DEVICE

FIELD OF THE INVENTION

The present invention relates to a silicon-on-insulator biosensor device. Specifically, the present invention allows for the identification of specific interactions between biomolecules in a highly parallel and highly sensitive way.

BACKGROUND OF THE INVENTION

Current techniques for protein detection, analysis and quantification include, e.g., two-dimensional gel electrophoresis combined with mass spectroscopy, micro-capillary electrokinetic separation techniques with fluorescent readout, micro-array analogs to DNA chip technology, and others like plasmon-resonance or quartz microbalance. In present micro-array approaches the underlying "chip" mostly consists of a surface functionalized plain glass substrate without any intrinsic function, detection hence relies solely on fluorescent labeling.

A common approach using silicon structures for the detection of biomolecular interactions is the use of capacitive measurements (Berggren et al., Electroanalysis 2001). Their usability is hampered by the need of highly insulating organic layers. Light addressable potentiometric sensors (LAPs) have also been proposed as a detection scheme (George et al., Sensors and Acuators, 2000). However, these approaches in general lack the sensitivity and universality. Also, standard FET structures were proposed for the use of biosensors, but lacked the necessary sensitivity as well (e.g. Schöning and Lüth, 2001). A further approach is the detection by means of mechanical strain, which has been used to detect the hybridization of DNA molecules (Fritz et al., Science, 2000). Another surface sensitive technique is the detection of surface plasmons, which is for example realised by the company Biocore.

Semiconductor devices to work as sensors in electrolyte environment such as ion sensitive FETs (ISFETs), mainly fabricated from standard Si substrates but also SOI have been reported and patented (e.g., W00051180). Various techniques have been reported in the field of antibody immobilization (e.g. DE10006760 A) for protein recognition on solid substrates. The first protein chip analog to DNA chips was realized recently (MacBeath G. and Schreiber S L, Science 2000). Cui et al. (Science 2001) demonstrated a functionalized nanostructure for model protein detection, the used Si nanowire however was manufactured in a complicated chemical deposition technique.

A technique directly using the electrical response of sensitive nanostructure devices upon the selective recognition or the detection of membrane proteins or other biomolecules, based on SOI, is not known to the authors.

The techniques currently used mostly suffer from the need to use optical detection. Fluorescent labeling in the case of commercial DNA chips is a rather mature technology. However, it introduces additional biochemical preparation steps, which results in the loss of significant parts of the material of interest. Especially in the labeling of proteins, as much as roughly 50% of the functional protein can be inactivated through the unspecific labeling procedures. This is a major drawback of these approaches, as especially for diagnostic purposes only very small quantities of the analyte are available.

All mentioned techniques based on silicon devices have resolution limits for very small protein concentrations. Proteins of most importance such as certain tumor markers are hardly been detected using the otherwise highly developed 2D electrophoresis technique.

SUMMARY OF THE INVENTION

An embodiment of the present invention is to provide for a semiconductor sensor device for the detection of target molecules and molecular interactions, based on Silicon-on-Insulator (SOI) technology.

This semiconductor sensor device is characterized by a metal gate-less field effect transistor (FET) fabricated from Silicon-on-Insulator (SOI) substrate material by standard, and advanced sub-$\mu$m lithographic, Silicon (Si) processing technology, the electronic conductivity in this transistor structure being restricted to a thin conductive surface-near sheet within the top Si layer, separated from bulk Si by the buried $SiO_2$ (BOX) and the FET being covered with a functional surface which may consist of, e.g., immobilized molecules.

This semiconductor sensor device is further characterized in that mobile carriers (electrons or holes) inside the top Si layer can be generated by impurity doping (e.g., epitaxial overgrowth, diffusion, implantation) or electrostatically induced from the device's backside (Si substrate), thus operating the device in an inverted FET mode.

This semiconductor sensor device is further characterized in that the sensitivity is increased and the region of detection is locally defined in form of sub-$\mu$m wires which may be formed by using, e.g., specific lithographic techniques such as electron-beam lithography or direct focused laser beam (FLB) oxidation to form in-plane-gate (IPG) transistor structures.

This semiconductor sensor device is further characterized in that the immobilized molecules may be biomolecules such as DNAs, antibodies, proteins and that for the functionalization of the surface, layers of immobilized organic molecules bound to the thin natural Si-Oxide top layer or other polymeric cushions, which inhibit unspecific interactions will be used.

This semiconductor sensor device further has the molecules, such as membrane proteins, are incorporated into a lipid bilayer membrane.

This semiconductor sensor device further has the binding of an analyte to this biofunctional sites changes the device's surface potential by three main contributions: Either 1) ionic charges of the molecule, or 2) the molecule's dipole moment or an binding-induced dipole, or 3) modification of energy distribution and/or density of surface states and in which any change of surface potential in turn leads to a change in the band structure and thus charge distribution in the semiconductor material directly changing the SOI layer's lateral conductivity.

This semiconductor sensor device further has the analyte target molecules are biomolecules such as DNA or proteins.

This semiconductor sensor device further has the analyte target species are ions in electrolyte solution (for, e.g., pH sensor operation).

This semiconductor sensor device further has the analyte target species are gas molecules.

This semiconductor sensor device further has the analyte target molecules do not have to be labeled.

This semiconductor sensor device further has the specific binding process can be observed in real-time.

This semiconductor sensor device further has at least two sensor units are arranged to an array where each unit is functionalized with individual receptor molecules to address ensembles of molecules in an analyte in parallel.

This semiconductor sensor device further is characterized in that the thickness of the top silicon layer is in the range of 20–150 nm, the buried $SiO_2$ (BOX) having a thickness of 50–500 nm, the bulk silicon substrate wafer having typical thickness of 0–800 $\mu$m.

BRIEF DESCRIPTION OF THE DRAWINGS

The foregoing and a better understanding of the present invention will become apparent from the following detailed description of exemplary embodiments and the claims when read in connection with the accompanying drawings, all forming a part of the disclosure of this invention. While the foregoing and following written and illustrated disclosure focuses on disclosing example embodiments of the invention, it should be understood that the same is by way of illustration and example only and the invention is not limited thereto. The spirit and scope of the present invention are limited only by the terms of the appended claims.

The following represents brief descriptions of the drawings, wherein.

DETAILED DESCRIPTION OF THE PREFERRED EMBODIMENTS

Figure 1:
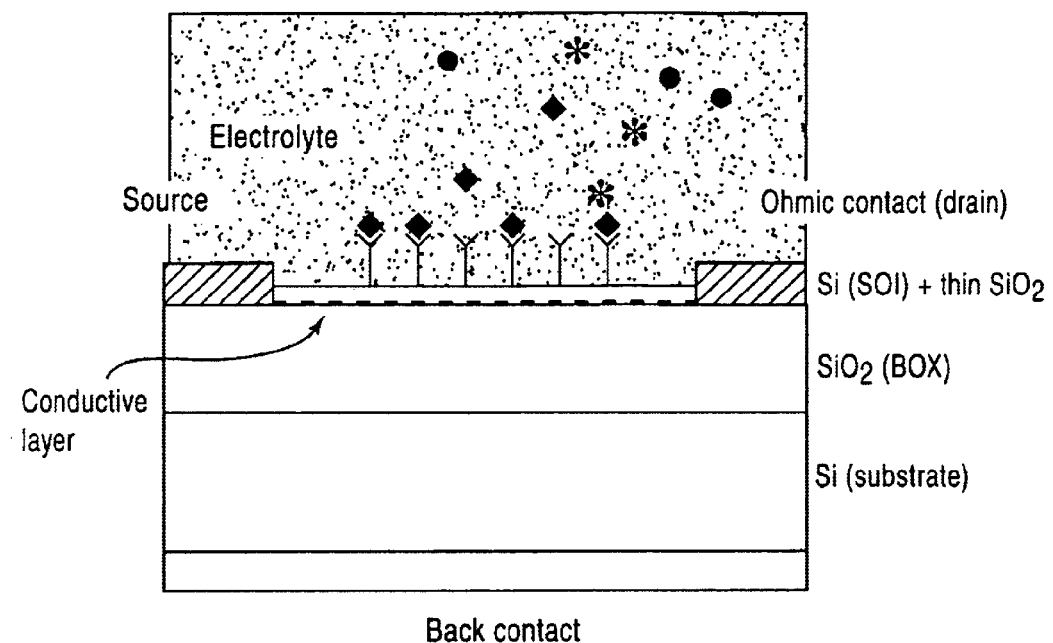
FIG. 1 shows a cross-sectional view of the substrate and the bio-functionalized silicon-on-insulator field effect transistor.

Before beginning a detailed description of the subject invention, mention of the following is in order. When appropriate, like reference numerals and characters may be used to designate identical, corresponding or similar components in differing figure drawings. Further, in the detailed description to follow, exemplary sizes/models/values/ranges may be given, although the present invention is not limited to the same.

Although recent progress in Genomics and Proteomics enables the purification of a huge number of different biomolecules, very few techniques are available to detect, analyse and quantify these species and their mutual interactions. Progress in the current biomedical research is relying on new universal tools, which allow the identification of specific interactions between biomolecules in a highly parallel and highly sensitive way.

The invention covers a semiconductor device for the detection of specific biomolecular interactions based on Silicon-on-Insulator (SOI) technology. The core device comprises a metal gate-less field effect transistor (FET) fabricated from Silicon-on-Insulator (SOI) substrate material by standard, and advanced sub-$\mu$m lithographic, Silicon (Si) processing technology. Electronic conductivity in this transistor structure is restricted to a thin conductive sheet within the top Si layer, separated from the surface by typically a few ten nm only and from the bulk Si by the buried $SiO_2$ (BOX). Mobile carriers (electrons or holes) inside this layer may be generated by impurity doping (epitaxial overgrowth, diffusion, implantation) or electrostatically induced from the device's backside (Si substrate), thus operating the device in an inverted FET mode. In contrast to standard FET technology however, the FET surface is not covered by a metal gate but instead with a biofunctional surface which may consist of, e.g., immobilized molecules such as single stranded DNAs, antibodies, proteins or molecules which are incorporated into a lipid bilayer membrane on top of the substrate. For the functionalization of the surface, layers of immobilized organic molecules bound to the thin natural Si-Oxide top layer or other polymeric cushions, which inhibit unspecific interactions will be used. Membrane proteins can be incorporated into solid supported lipid bilayers.

Binding of an analyte to this biofunctional sites may change the device's surface potential by three main contributions: 1) Ionic charges of the molecule 2) The molecule's dipole moment or an binding-induced dipole 3) Modification of energy distribution and/or density of surface states. Any change of surface potential in turn leads to a change in the band structure and thus charge distribution in the semiconductor material directly changing the SOI layer's lateral conductivity because of its close proximity to the surface this effect is highly sensitive to even minor changes in surface potential. To increase the sensitivity and at the same time miniaturize the active device region SOI sub-$\mu$m to nano-nm wires can be formed by using specific lithographic techniques such as electron-beam lithography or direct focused laser beam (FLB) oxidation to form in-plane-gate (IPG) transistor structures (M. Huber et al., Applied Surface Science 2000). In such IPGs the effective electrical wire width and its mean carrier concentration can be electrostatically tuned by applying a voltage to the electrically separated in-plane SOI regions (gates) alongside, thereby adjusting the device's performance. By combining many such (IPG-) FET units to whole arrays and functionalizing them with individual receptor molecules using lithographic techniques, whole ensembles of molecules in an analyte may be detected in parallel. Important examples for possible applications are the detection of protein expression patterns by using antibodies as capturing receptors, the detection of gene expression patterns by gene arrays consisting of immobilized single stranded DNA molecules, the detection of protein-protein interactions consisting of immobilized proteins and the binding and clustering of membrane proteins. Consequences of the applications for diagnostic purposes are manifold and the highly parallel detection will enable also the application of this biosensor in pharmaceutical research.

The SOI biosensor device allows the label-free, highly sensitive, local and real-time sensing of the selective binding of bio-molecules. A SOI chip comprising of an array of individually functionalized transistors addresses the parallel detection, identification and quantification of e.g. thousands of proteins in one sample. The chip can be integrated in Si standard integrated circuit process technology thus being compatible to cost efficient high-volume industrial production. The novel technique has applications in diagnostics, drug development and research.

Other more general applications are chemical sensing such as ion-sensitive FET (ISFET, pH meter) operation and gas molecule sensing for, e.g., food and environmental control purposes.

The main novelty of the described invention is the direct application of a (sub-$\mu$m sized) electronically active semiconductor "smart substrate" for biochip applications. In contrast to the commonly used passive e.g. glass substrates here, a highly sensitive semiconductor transistor device comprising of a ultra surface-near conductive channel within a SOI structure allows the direct detection of bio-molecules and their mutual interactions by purely electrical readout. This is in sharp contrast to the commonly used approach of capacitive measurements and also of traditional FET structures. The main advantages are 1) label-free detection 2) miniaturization for high-throughput parallel analysis 3) tunable high sensitivity 4) integration into current commercial semiconductor process technology. Selective binding reactions from analytes to immobilized receptors (such as ss-DNA, antibodies, proteins) can be detected.

In first experiments, prototype devices have been processed. In these prototypes, the substrate consisted of a 650 μm silicon handle wafer covered by a 200 nm $SiO_2$ BOX layer, followed by the sensing single-crystal SOI layer. This layer either consisted of a pure, undoped 30 nm thick Si layer or the same, but additionally overgrown with a 50 nm highly p-type doped silicon layer (Boron, $10^{19}$ $cm^{-3}$), by molecular beam epitaxy. The whole structure was covered by the native oxide layer of 1–2 nm thickness.

The substrates were patterned by standard photolithographic techniques (SOI mesa wet etching, AlAu ohmic contacts HV evaporation and alloying), and subsequently characterized in a standard 4-terminal lateral resistance measurement. In first experiments, the device's electrical response upon changes of the ionic strength in aqueous electrolyte buffer solutions was determined.

These preliminary experiments demonstrate the devices high sensitivity to changes in the electrolyte solution. The results can be explained in a model taking into account the change of surface potential. Furthermore, prototype chips have been functionalized with amino-propyl-triethoxysilane in order to realize a pH sensitive device. The covalent binding of the bioactive molecule is achieved through a siloxane linkage. Another approach for the functionalization is the physisorption of a polymer layer, such as functionalized (BSA) molecules. So far it has been shown that already functionalizing the device drastically reduces the conductivity of the SOI layer which can be explained by the expected changes of the surface state configuration. Experiments to detect the change of the surface potential of functionalized surfaces by the pH of different solutions are ongoing.

Embodiments of the Invention are Described in Connection with the Attached Figures:

FIG. 1 shows a cross-sectional view of the substrate and the bio-functionalized silicon-on-insulator field effect transistor. Current flows from the source to the drain contact through a thin conductive sheet within the top silicon layer. The conductivity in this sheet is affected by the specific binding of charged molecules to molecular receptors which are immobilized on the surface.

Figure 2:
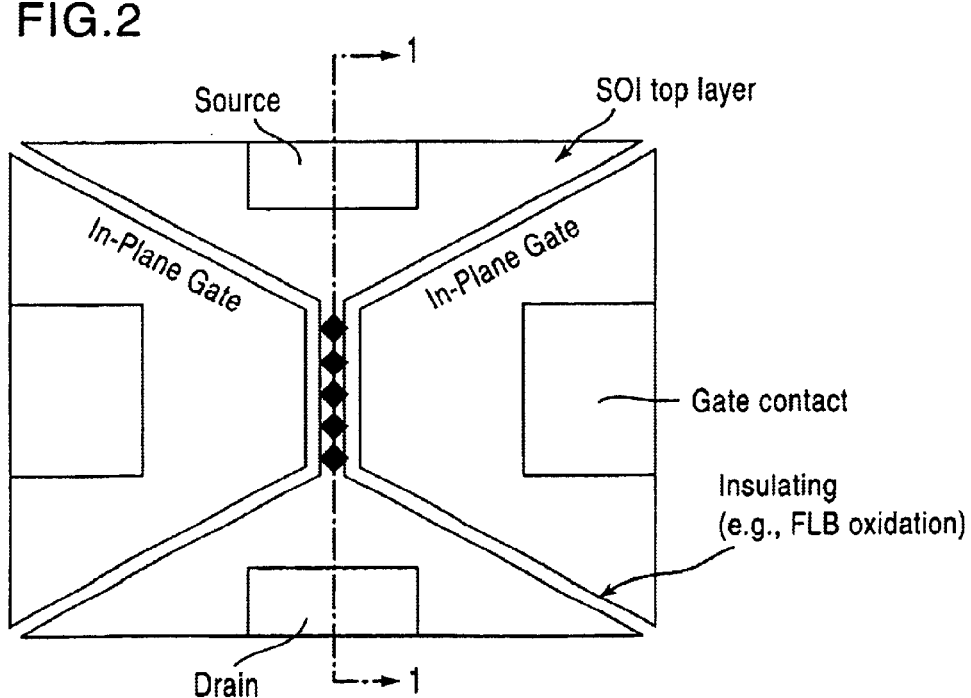
FIG. 2 shows a top view of a possible In-Plane-Gate transistor design.

FIG. 2 shows a top view of a possible In-Plane-Gate transistor design. The active channel is electrically separated from two gates which are located in the same plane as the conducting channel by, e.g., direct focussed laser beam writing. An electric field due to a certain voltage between gates and conductive channel changes the channel's effective width and thus the current passing at a preset source-drain voltage. Hence the sensitivity to an alteration of the conductivity by molecules binding to the surface can be maximized. A cross-sectional view along the dashed line is shown in FIG. 1.

Figure 3A:
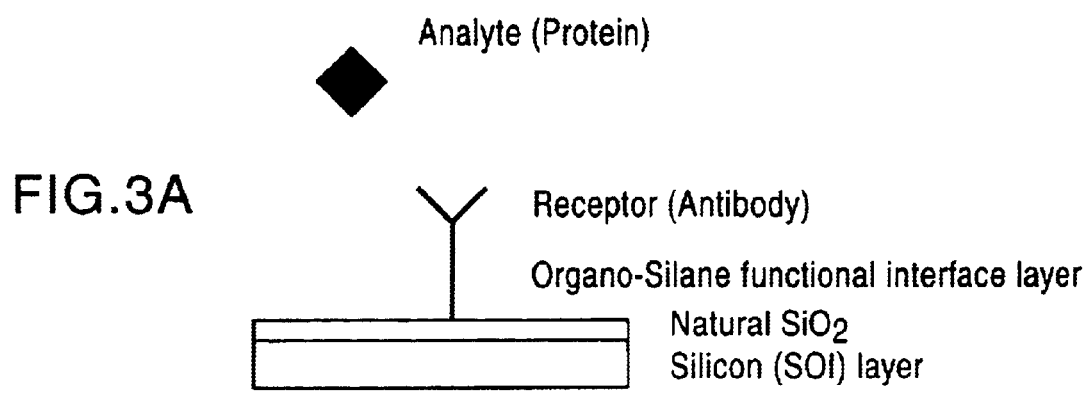
FIG. 3A shows a schematic representation of the bio-functionalization of the substrate.

FIG. 3A shows a schematic representation of the bio-functionalization of the substrate. Bio-organic molecules, e.g. receptors or antibodies, are immobilized on top of the natural silicon dioxide layer via an interlayer (e.g., silane linker, see FIG. 3B). Analyte molecules (e.g., proteins) passing the surface bind to the appropriate antibodies and thus can be detected by a shift of the electrical surface potential. Possible mechanism include: ionic charges of the analyte, an altered dipole moment after binding, the modification of the energy distribution and/or density of surface states. This shift alters the band structure of the semiconductor and thus changes the charge carrier concentration which can be directly measured via the conductivity of the SOI layer.

Figure 3B:
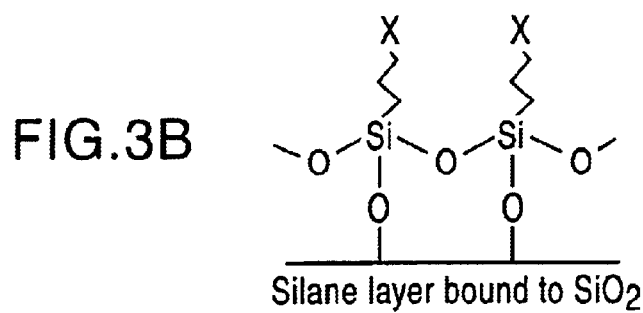
FIG. 3B shows the silane layer bound to $SiO^{2-}$

FIG. 3B shows a detailed illustration of the binding sites on the silicon dioxide surface. Silanes (Si-terminated alkane chains of variable length) are bound to one of the four bonds of a Si atom at the surface. The silanes are modified with functional endgroups (symbolized by the X) at the other end prior to the surface modification. These endgroups can be specific receptor molecules such as antibodies.

Figure 4A:
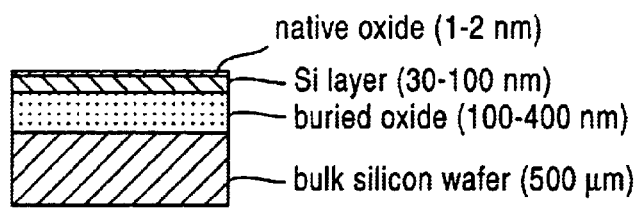
FIG. 4A shows a schematic view of the SOI substrate.

FIG. 4A shows a schematic view of the SOI substrate. The SOT substrate embodies a buried silicon dioxide (BOX) layer which electrically separates the Si bulk handle wafer from the top Si layer (containing the electrically active channel) which in turn is covered by a thin, natural silicon dioxide layer.

Figure 4B:
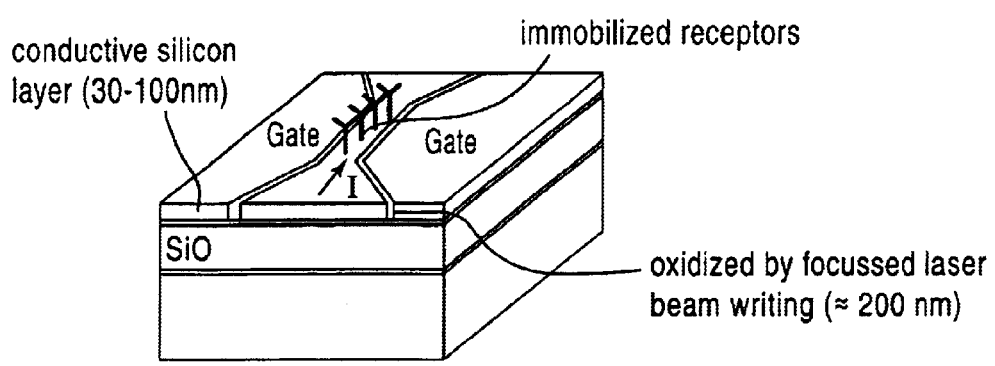
FIG. 4B shows a sensing "nano"-structure.

FIG. 4B shows a three-dimensional sketch of the SOI sensor nanostructure (in-plane-gate field effect transistor), compare FIG. 2. Electrical separation of the channel from the gates can be achieved by focussed laser beam oxidation or, based on electron beam lithography.

Figure 5:
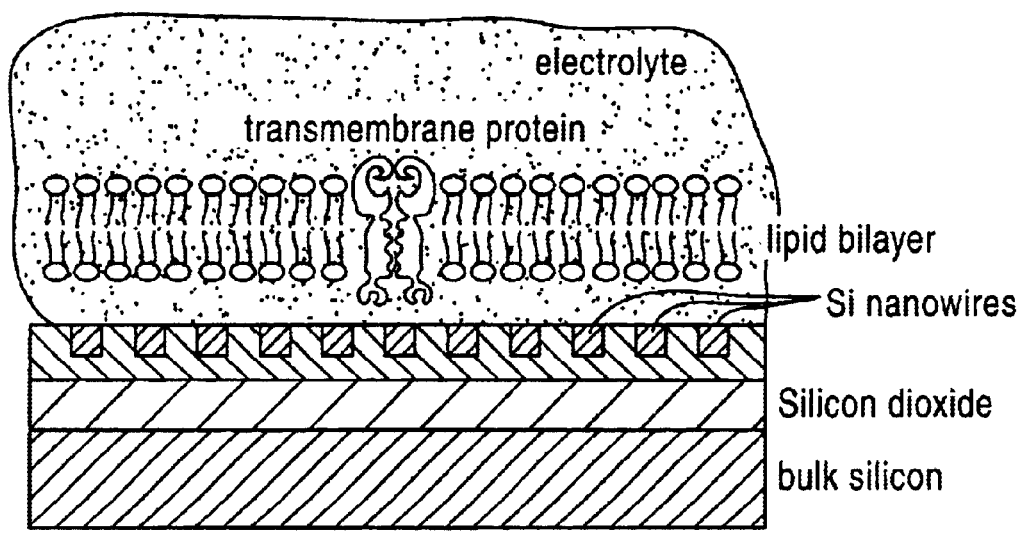
FIG. 5 shows a schematic view (cross section) of a laterally patterned SOI substrate.

FIG. 5 shows a schematic view (cross section) of a laterally patterned SOI substrate. By using, e.g., focussed laser beam assisted oxidation, many parallel nanowires can be defined. The presence of biomolecules at the surface of the device, e.g., a membrane bound protein can therefore be detected with high spatial resolution and hence enables the parallel readout of many interactions in parallel.

While we have shown and described only a few examples herein, it is understood that numerous changes and modifications as known to those skilled in the art could be made to the present invention. Therefore, we do not wish to be limited to the details shown and described herein, but intend to cover all such changes and modifications as are encompassed by the scope of the appended claims.

We claim:

1. A semiconductor sensor comprising:
   a Silicon-on-Insulator (SOI) substrate comprising a top silicon layer an a silicon oxide ($SiO_2$) layer underneath;
   a channel being formed on said Silicon-on-Insulator substrate and connecting a source and a drain;
   characterized by
   a functional surface covering said top silicon layer over said channel; and
   a gate laterally separated from said channel by a barrier.

2. The semiconductor sensor according to claim 1, wherein said barrier consists of silicon oxide ($SiO_2$) formed in said top silicon layer.

3. The semiconductor sensor according to claim 1, wherein said gate is laterally separated by said barrier from said source and said drain.

4. The semiconductor sensor according to claim 1, comprising a further gate opposite to said gate laterally separated from said channel by a barrier.

5. The semiconductor sensor according to claim 2, wherein said silicon oxide ($SiO_2$) barrier formed in said top silicon layer is formed by direct focused laser beam (FLB) oxidation.

6. The semiconductor sensor according to claim 1, wherein the width of said channel is in the nm to sub-$\mu$m range.

7. The semiconductor sensor according to claim 1, wherein said top silicon layer is in the range of 20 to 150 nm.

8. The semiconductor sensor according to claim 1, wherein the electrical properties of said top silicon layer are determined by epitaxial overgrowth.

9. The semiconductor sensor according to claim 1, wherein said silicon oxide ($SiO_2$) is in the range of 50 to 500 nm.

10. The semiconductor sensor according to claim 1, wherein a bulk silicon substrate having a thickness of up to 800 $\mu$m is situated underneath said silicon oxide ($SiO_2$) layer.

* * * * *

UNITED STATES PATENT AND TRADEMARK OFFICE
CERTIFICATE OF CORRECTION

PATENT NO. : 6,870,235 B2
DATED : March 22, 2005
INVENTOR(S) : Abstreiter et al.

It is certified that error appears in the above-identified patent and that said Letters Patent is hereby corrected as shown below:

<u>Title page,</u>
Item [30], Foreign Application Priority Data,
Change "May 15, 2002     (DE) ............... 102 21 799" to be
-- May 15, 2002     (DE) ............... 102 21 799.8 --.

Signed and Sealed this

Sixth Day of September, 2005

JON W. DUDAS
*Director of the United States Patent and Trademark Office*